United States Patent [19]

Sears

[11] Patent Number: 4,507,217

[45] Date of Patent: Mar. 26, 1985

[54] MAGNETIC COMPOSITIONS AND MAGNETIC MEMORY DEVICES PREPARED THEREFROM

[75] Inventor: Barry D. Sears, Marblehead, Mass.

[73] Assignee: Lipid Specialties, Inc., Cambridge, Mass.

[21] Appl. No.: 493,928

[22] Filed: May 12, 1983

Related U.S. Application Data

[63] Continuation-in-part of Ser. No. 472,481, Mar. 7, 1983, which is a continuation-in-part of Ser. No. 284,675, Jul. 20, 1981, Pat. No. 4,426,330.

[51] Int. Cl.$^3$ .......................... C04B 35/04; C07F 9/02
[52] U.S. Cl. .................. 252/62.54; 360/134; 365/171
[58] Field of Search ..................... 252/62.54; 365/171; 360/134

[56] References Cited

U.S. PATENT DOCUMENTS

| | | | |
|---|---|---|---|
| 4,018,967 | 4/1977 | Roller et al. | 252/62.54 |
| 4,018,968 | 4/1977 | Neumann et al. | 252/62.54 |
| 4,097,617 | 6/1978 | Datta | 252/62.54 |
| 4,197,357 | 4/1980 | Huisman | 252/62.54 |
| 4,369,230 | 1/1963 | Kimura et al. | 252/62.54 |
| 4,404,260 | 9/1983 | Shibata | 252/62.54 |
| 4,426,330 | 1/1984 | Sears | 260/403 |
| 4,464,279 | 8/1984 | Arai | 252/62.54 |
| 4,465,608 | 8/1984 | Gerüm et al. | 252/62.54 |

*Primary Examiner*—Arthur P. Demers
*Attorney, Agent, or Firm*—Richard P. Crowley

[57] ABSTRACT

Liquid magnetic compositions suitable for use in coating a substrate, such as a tape or a disc, for the preparation of magnetic memory devices, which liquid composition comprises finely-divided magnetic particles, optionally a binder for the magnetic particles, a dispersing agent for the magnetic particles and a volatile liquid solvent, the dispersing agent comprising a synthetic phosphatidyl ethanolamine polymer.

16 Claims, No Drawings

MAGNETIC COMPOSITIONS AND MAGNETIC MEMORY DEVICES PREPARED THEREFROM

REFERENCE TO PRIOR APPLICATIONS

This application is a continuation-in-part of U.S. application Ser. No. 472,481, filed Mar. 7, 1983, which application is a continuation-in-part of U.S. application Ser. No. 284,675, filed July 20, 1981, now U.S. Pat. No. 4,426,330, both of which applications are hereby incorporated by reference in their entirty.

BACKGROUND OF THE INVENTION

Magnetic memory devices are prepared by coating, impregnating or otherwise placing a magnetic composition containing finely-divided magnetic particles onto a substrate, such as a flexible or solid substrate, to prepare a magnetic memory device which is capable of storing and retrieving information. Typical magnetic memory devices would include, but not be limited to, rigid-type devices which may comprise a hard disc composed of a nonmagnetic material, such as aluminum or flexible-type devices which typically would include a floppy disc or a tape composed, for example, of a polyester or other plastic material, and typically Mylar, such as in use for audio tapes, computer tapes or floppy discs. Thus, for example, in the preparation of magnetic tapes, a liquid magnetic composition is coated or impregnated onto a plastic, paper or metal tape, with the magnetic composition containing magnetizable iron oxide particles of single- or multiple-domain magnetic particles which do not lose memory in absence of a magnetic field. In one method of preparation, a liquid magnetic composition is cast or coated onto a polyester film-like material as a wet, controlled solvent-type coating of a thin thickness; for example, 1/10th to 3 mils, and the volatile solvent material is driven off, to provide for a magnetic coating on the substrate surface.

A typical liquid magnetic composition, suitable for use in preparing magnetic memory devices for storage and retrieval of information, would include magnetic compositions which contain finely-divided magnetic particles. These particles, while they may be agglomerated in larger size, typically have a particle size ranging from an average particle size of about 1000 up to 10,000 Angstroms. The magnetic particles may comprise a wide variety of magnetic elements of iron, nickel and cobalt or alloys, and may comprise iron oxide, chromic oxide, barium ferrite, iron particles themselves and various mixtures and alloys thereof, together with various additives.

The magnetic composition also usually includes a small amount ranging from about 0.5% to 5% by weight; for example, about 3% to 4% by weight, of the solids content of the magnetic composition, of a dispersing agent or primary surfactant. One dispersing agent or surfactant in widespread use in the preparation of a liquid magnetic composition comprises deoiled lecithin, which is a mixture of natural phospholipids. The liquid magnetic composition also usually contains an amount of a binder-type material, typically a polymeric-type nonmagnetic binder, such as a urethane or other resin, and usually an elastomeric urethane resin capable of being cross-linked, the binder material adapted to bind the separated finely-divided oxide particles into position and to bind the magnetic oxide particles to the substrate. The amount and nature of the binder material may vary and generally comprise from 5% to 40% by weight of the total solids, and more typically 18% to 35% by weight. Various other additives and modifiers may be added to the magnetic composition as desired, which additives or modifiers include, for example, particulate material to reduce electrostatic charge, such as finely-divided carbon-black material usually in an amount of from about 0.1% to 4% by weight of the solids, and more typically 1.5% to 2.5% by weight. Another modifier includes a lubricant-type material ranging generally from as low as 1% to as high as 8% by weight of the total solids; for example, 2% to 4% by weight, and which may comprise silicones and more typically fatty-acid-type materials like fatty-acid soaps and particularly alkyl stearates and oleates, such as isobutyl stearate. Other additives and modifiers may be used as required, depending upon the nature, type and ultimate use of the magnetic composition.

The magnetic compositions are prepared by placing the ingredients together with a suitable solvent or mixture of solvents and diluents, and more generally volatile organic solvents and diluents, in a ball mill or sand mill. A variety of solvents may be employed, but generally an organic volatile solvent is used, to provide a liquid medium for dispersion of the magnetic particles in the solvent and diluent, and which solvent mixture provides for the solubilization of the binder material and the dispersing agent. Typical solvents and diluents would include benzene, toluene, cyclohexanone, methylethyl ketone, methylisobutyl ketone, dimethyl formamide or tetrahydrofuran alone or in various solvent mixtures. The particulates in the magnetic composition are then dispersed through the use of ball milling, sand milling, ultrasonics or other dispersing-type techiques, so as to provide for the generally uniform dispersion of the finely-divided magnetic particles and to break up the agglomeration of the particles and to disperse any other pigments or particles in the magnetic composition. After the dispersion, the liquid magnetic composition so prepared is then coated or impregnated onto a substrate surface, and the organic solvent and diluents are driven off by heat, to provide a dried coating layer containing the magnetic particles.

Thus, a typical formulation for the preparation of a magnetic composition for use on a substrate, to prepare a memory storage device comprises:

| | | |
|---|---|---|
| Magnetic metal, metal oxide or alloy | 10–400 | grams |
| Dispersing agent | 1–40 | grams |
| Binder | 5–300 | grams |
| Solvent | 5–200 | ml |

This mixture is dispersed by a grinding operation, and the mixture is then applied to a subtrate surface using various coating and impregnating techniques, such as spin or web coating.

While prior-art techniques and compositions are satisfactory, it is desirable to prepare new and improved liquid magnetic compositions and to prepare magnetic memory devices therefrom which have improved magnetic and other properties, particularly magnetic storage devices which have improved response of the magnetic particles in a magnetic field, so as to obtain or approach a rectangular hysteresis loop.

SUMMARY OF THE INVENTION

The invention relates to a new liquid magnetic composition and to a method of preparing such magnetic composition and of preparing magnetic memory devices employing such magnetic composition and to the devices so prepared. In particular, the invention relates to a magnetic composition containing a new and effective dispersing agent for the finely-divided magnetic particles which provides for magnetic memory devices of improved magnetic properties.

It has been discovered that synthetic phospholipids are remarkably more active and unexpectedly effective than the present dispersing agents employed in dispersing magnetic particles or magnetic storage devices, such as deoiled soy lecithin. The novel synthetic phospholipids provide for a far higher degree of solubilization and dispersion properties than natural lecithin or the isolated phospholipids; that is, phosphatidylcholine, phosphatidylethanolamine, phosphatidylinositol or phosphatidic acid, all of which comprise soy lecithin, the typical dispersing agent used in prior-art magnetic compositions. The synthetic phospholipid polymers employed as a dispersing agent in the invention provide for far more effective dispersing of the finely-divided magnetic particles in the magnetic composition, and, further, result in magnetic memory devices of considerably enhanced and improved magnetic properties. Thus, it has been found that the magnetic particles employed in the magnetic compositions are not only dispersed more effectively and more rapidly employing the synthetic phospholipid polymers, but also provide for superior magnetic properties relative to the magnetic particles dispersed with deoiled lecithin or other dispersing agents and often permit a reduction in amount of the binder.

The synthetic phospholipids useful as a dispersing agent in the magnetic composition of the invention include those phospholipids having the following general structural formula:

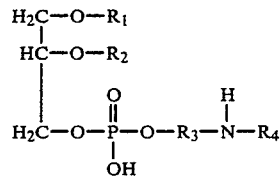

wherein $R_1$ and $R_2$ are acyl radicals or hydrogens; $R_3$ is a polymethylene radical; that is, $-\!\!-\!(CH_2)_n\!\!-\!\!$, where n may be 2 to 10 or more, and more particularly an ethylene radical; and $R_4$ is a long-chain polymeric radical typically containing one or more carboxylic acid groups, to form an amide radical with the NH radical

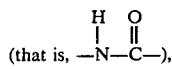

and more particularly a carboxylic polyalkylene oxide radially, or may represent a direct covalent bond; that is, $-N-C-$, to form the polymer radical.

Particular synthetic phospholipid polymers useful as dispersing agents include, but are not limited to, the phosphatidyl alkanolamine carboxyl polyalkylene oxide phospholipids described in U.S. Ser. No. 284,675, filed July 20, 1981, such as phosphatidyl ethanolamine carboxyl polyethylene oxide phospholipids, and having the structural formula:

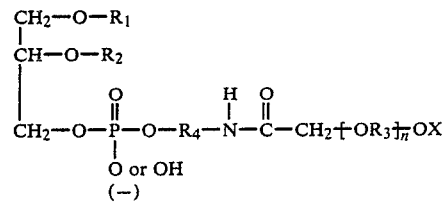

wherein $R_1$ and $R_2$ are hydrogens or acid groups, such as saturated or unsaturated straight or branch organic acyl groups, such as $C_2$-$C_{25}$ fatty-acid radicals; for example, $C_{12}$-$C_{18}$ fatty-acid radicals as found, for example, in vegetable; for example, soy, animal, egg, yeast or bacterial; for example, gram positive, phospholipids, to include fatty-acid radicals of lauric, myristic, linoleic, palmitic, palmoleic, stearic, oleic, etc. groups; $R_3$ represents an alkylene group, particularly an ethylene or propylene group; $R_4$ represents a polymethylene group, such as a $C_2$-$C_{10}$ polymethylene and particularly an ethylene (dimethylene) or propylene (trimethylene) group; and X is a hydrogen or an alkyl group, such as a $C_1$-$C_4$ group like a methyl group. The number of $C_2$-$C_3$ alkylene $R_3$ groups may vary from 0 to 200 or more; for example, 2 to 30. The molecular weight of the phospholipid generally may range from about 750 to 9000; for example, 850 to 1500. These phospholipids are prepared by covalently coupling a carboxylic analog of a polyalkylene oxide polymer, such as a polyethylene oxide, to a phosphatidyl alkanolamine like a soy or bacterial phosphatidylethanolamine. The carboxylic analog is prepared by oxidizing the polyalkylene glycol used in the coupling reaction.

Another class of synthetic phospholipids useful as dispersing agents include, but are not limited to, phosphatidyl alkanolamine polycarboxyl polyalkylene glycol compounds, such as phosphatidylethanolamine di or tri carboxyl polyethylene or polypropylene glycol compounds, as described in U.S. Ser. No. 472,481, filed Mar. 7, 1983, having the general structural formula:

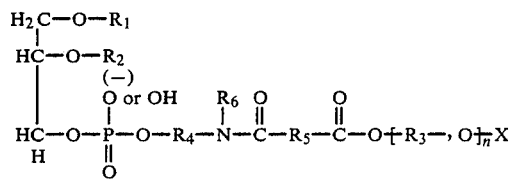

where $R_1$, $R_2$, $R_3$, and $R_4$ have the same definitions as before and wherein $R_6$ is hydrogen or an alkyl group like methyl and $R_5$ is an organic linking radical; for example, a hydrocarbon radical, of from about 1 to 24 carbon atoms, but typically from about 2, 3 or 4 carbon atoms, which radial may be saturated or unsaturated, may be substituted, for example, with hydroxyl, amino or carboxyl groups, or be an unsubstituted radical, such as a polymethylene ($-CH_2-$) radical like an ethylene, propylene or butylene radical.

These polycarboxylic phospholipids are prepared by employing a di or tri carboxylic acid, typically a succinic or glutaric acid anhydride, to couple the polyalkylene oxide and the phosphatidylethanolamine derived, for example, from soy or bacterial; for example, gram positive, phospholipids. Typical specific phospholipids comprise soy phosphatidyl ethanolamine succinyl polyethylene glycol monomethyl ether (MW 120) and soy phosphatidyl ethanolamine glutaryl polyethylene monomethyl ether (MW 252).

The synthetic phospholipids useful as dispersing agents may be employed in the same general amounts as the prior-art dispersing agents or, due to their enhanced dispersing properties, in lower amounts and in an amount sufficient to provide the desired dispersion of the magnetic particles.

For the purpose of illustration only, the invention will be described in connection with certain particular embodiments for particular synthetic phospholipids; however, it is recognized that those persons skilled in the art may make various modifications, changes and additions to the compositions and the method of preparing the same as illustrated, all without departing from the spirit and scope of the invention.

DESCRIPTION OF THE EMBODIMENTS

EXAMPLE 1.

20 g of a 1000Å-diameter magnetic metal oxide, 15 g of CA-276 polyurethane (Morton Chemical) as a binder and 1 g of soy phosphatidyl ethanolamine monomethyl ether polyethylene oxide (average molecular weight 564 (that is, PX564)) as a dispersing agent were placed in a 4-inch-diameter glass ball mill with 100 g of ¼th inch stainless-steel balls. 100 ml of DMF were added and the mixture was allowed to grind on a roller mill. Similar conditions were employed for a companion sample, except that 1 g of deoiled lecithin (Centrolex-R, Central Soya) was substituted as a dispersing agent for the synthetic phospholipid. After 5 days of grinding at room temperature, various magnetic properties were measured, employing a B-H meter of the resulting magnetic composition, with the results shown in Table I.

TABLE I

| Dispersing Agent | $H_c$ | $S_q$ |
| --- | --- | --- |
| PX564 | 535 | 0.48 |
| Deoiled lecithin | 510 | 0.22 | where $H_c$ is the coercivity in orestads and $S_q$ is a figure of merit relating to the squareness of the hystersis curve and is determined by the formula $S_q = B_r/M_s$, wherein $B_r$ is the remanence at zero magnetic field and $M_s$ is the magnetism at saturation. The magnitude of $S_q$, which has a maximum theoretical value of 1, is the significant magnetic property which measures the response of the magnetic particles in a magnetic field and where high values are desired.

EXAMPLE 2.

To 20 g of a 1000Å-diameter magnetic metal oxide and 0.1 g of surfactant were added 100 ml of tetrahydrofuran. The dispersing agents used were either deoiled soy lecithin (Centrolex-R, Central Soya) or soy phosphatidyl ethanolamine polyethylene oxide monomethyl ether (average molecular weight 564 (that is, PX564)). Each mixture was placed into a ceramic jar mill (4-inch diameter) containing 500 g of ¼th-inch-diameter stainless-steel balls. The mill was sealed and placed on a roller at a speed of 136 r.p.m. Samples of each dispersion were taken daily and various magnetic properties were measured, with the results shown in Table II.

TABLE II

| Dispersing Agent | $H_c$ | $S_q$ |
| --- | --- | --- |
| Deoiled soy lecithin | | |
| 2 days | 677 | .28 |
| 3 days | 713 | .35 |
| PX 564 | | |
| 1 day | 840 | .75 |

The large increase in the $S_q$ and $H_c$ of the PX 564, relative to the Centrolex-R formulation, is an indication of the superior and unexpected dispersing ability of the synthetic phospholipid polymer, both in terms of the magnetic properties of the dispersion and the rate at which those magnetic properties are achieved in the preparation of the dispersion.

EXAMPLE 3.

A magnetic tape useful for the recording and storing of information is prepared by reverse roll-coating a thin layer of the magnetic composition PX 564 of Examples 1 and 2 onto a substrate, such as a Mylar film, heating the thin layer to remove the organic solvent and recovering a memory storage device.

What is claimed is:

1. In a magnetic composition suitable for use in preparing magnetic memory devices, which magnetic composition comprises finely-divided magnetic particles, a dispersing agent for the magnetic particles and a solvent, the improvement which comprises employing as the dispersing agent a synthetic phospholipid having the structural formula:

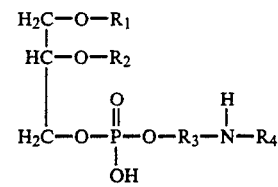

wherein $R_1$ and $R_2$ are hydrogen or acyl radicals, $R_3$ is a polymethylene radical and $R_4$ is a long-chain polymer radical which provides an

or an N-C bond.

2. The composition of claim 1 wherein $R_3$ is an ethylene radical.

3. The composition of claim 1 wherein $R_1$ and $R_2$ are $C_2$-$C_{25}$ organic fatty-acid radicals.

4. The composition of claim 1 wherein $R_4$ is a carboxyl polyalkylene oxide radical.

5. The composition of claim 1 wherein $R_4$ is a monocarboxyl polyethylene oxide radical.

6. The composition of claim 1 wherein the phospholipid is a phosphatidyl ethanolamine carboxyl polyethylene oxide monomethyl ether.

7. The composition of claim 1 wherein the phospholipid is a phosphatidyl ethanolamine succinyl or glutaryl polyethylene glycol monomethyl ether.

8. The composition of claim 1 wherein the solvent comprises dimethyl formamide or tetrahydrofuran.

9. The composition of claim 1 wherein the magnetic particles have an average diameter of from about 1000 to 10,000 Angstroms.

10. The composition of claim 1 which includes a binder resin, wherein the binder is a polyurethane resin.

11. The composition of claim 1 wherein the magnetic particles comprise magnetic metal or metal oxide particles.

12. A magnetic memory storage device which is prepared employing the composition of claim 1.

13. A magnetic memory storage device which contains a magnetic coating prepared by the composition of claim 6.

14. In a magnetic composition suitable for use in preparing magnetic memory devices, which magnetic composition comprises finely-divided magnetic particles, a binder for the particles, a dispersing agent for the magnetic particles and a solvent, the improvement which comprises employing as the dispersing agent a synthetic phospholipid having the structural formula:

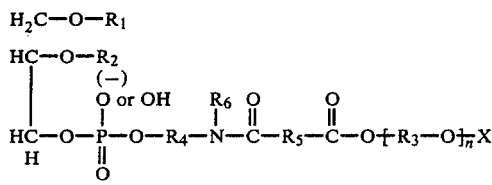

wherein $R_1$ and $R_2$ are acyl radicals or hydrogen, $R_3$ is a polyethylene radical, $R_4$ is a polymethylene radical, $R_5$ is an organic linking radical, $R_6$ is a hydrogen or an alkyl group, n is a number from 0 to 200 and X is a hydrogen or alkyl group.

15. In a magnetic composition suitable for use in preparing magnetic memory devices, which magnetic composition comprises finely-divided magnetic particles, a binder for the particles, a dispersing agent for the magnetic particles and a solvent, the improvement which comprises employing as the dispersing agent a synthetic phospholipid having the structural formula:

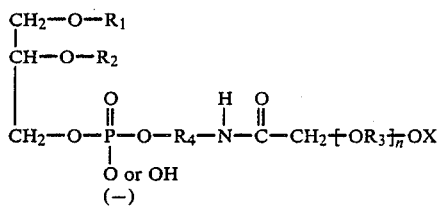

wherein $R_1$ and $R_2$ are acyl radicals or hydrogen, $R_3$ is a polyethylene radical, $R_4$ is a $C_2$-$C_{10}$ radical, n is a number from 0 to 200 and X is a hydrogen or alkyl group.

16. A magnetic memory storage device which contains as a dispersing agent a synthetic phosphatidyl ethanolamine carboxyl polyethylene oxide polymer.

* * * * *